United States Patent
Matsumoto (10) Patent No.: US 10,814,094 B2
(45) Date of Patent: Oct. 27, 2020

(54) METHOD FOR ACHIEVING THE BALANCE OF THE MIND

(71) Applicant: Miross Institute Co., Ltd, Ashiya-Shi, Hyogo (JP)

(72) Inventor: Hiroshi Matsumoto, Ashiya (JP)

(73) Assignee: MIROSS INSTITUTE CO., LTD., Ashiya-Shi (JP)

( * ) Notice: Subject to any disclaimer, the term of this patent is extended or adjusted under 35 U.S.C. 154(b) by 720 days.

(21) Appl. No.: 15/184,297

(22) Filed: Jun. 16, 2016

(65) Prior Publication Data

US 2017/0361059 A1    Dec. 21, 2017

(51) Int. Cl.
| | |
|---|---|
| A61M 21/02 | (2006.01) |
| A61B 5/16 | (2006.01) |
| G09B 5/04 | (2006.01) |
| G09B 5/02 | (2006.01) |
| G09B 19/00 | (2006.01) |
| A61M 21/00 | (2006.01) |
| G09B 7/00 | (2006.01) |

(52) U.S. Cl.
CPC ............ *A61M 21/02* (2013.01); *A61B 5/165* (2013.01); *G09B 5/02* (2013.01); *G09B 5/04* (2013.01); *G09B 19/00* (2013.01); *A61M 2021/0044* (2013.01); *A61M 2205/502* (2013.01); *G09B 7/00* (2013.01)

(58) Field of Classification Search
CPC ............ A61M 21/02; A61M 2205/502; A61M 2021/0044; A61B 5/165; G09B 5/04
See application file for complete search history.

(56) References Cited

U.S. PATENT DOCUMENTS 5,213,562 A    5/1993    Monroe

OTHER PUBLICATIONS

Don Miguel Ruiz. The Four Agreements: A Practical Guide to Personal Freedom. Nov. 7, 1997.*
https://www.wikihow.com/Read-Tarot-Cards Published Jun. 2, 2015. Accessed Oct. 10, 2019 (Year: 2015).*
Tarot Software for windows 95—Amazon.com. Accessed Oct. 10, 2019 (Year: 1998).*
https://science.howstuffworks.com/science-vs-myth/extrasensory-perceptions/tarot-card6.htm How Tarot Cards Work. Lee Ann Obringer. Published Jan. 2, 2102. Accessed Oct. 10, 2019 (Year: 2012) (intro page).*
https://science.howstuffworks.com/science-vs-myth/extrasensory-perceptions/tarot-card6.htm How Tarot Cards Work. Lee Ann Obringer. Published Jan. 2, 2102. Accessed Oct. 10, 2019 (Year: 2012) (Spread Page).*

* cited by examiner

*Primary Examiner* — Christine H Matthews
*Assistant Examiner* — Joshua Daryl D Lannu
(74) *Attorney, Agent, or Firm* — McCarter & English, LLP (57) ABSTRACT

This invention relates to a method for achieving the balance of the mind of an examinee, the method comprising a first step of showing a set of symbols to an examinee; a second step of applying the symbols to a feeling of the examinee and a state of the examinee's mind; a third step of making the examinee understand a recognition system represented by the set; and a fourth step of resolving a conflict in the examinee's mind to achieve the balance of the examinee's mind; the set including a first to seventh symbols 1 to 7.

15 Claims, 9 Drawing Sheets

| List up | Before*1 | After | Test value | Significance probability | Number of components in category | Number of components |
|---|---|---|---|---|---|---|
| 1 | oneself | N.D. | 4.31 | 0 | 15 | 42 |
| 2 | partner | N.D. | 2.93 | 0 | 6 | 14 |
| 3 | relationship | N.D. | 2.74 | 0 | 4 | 7 |
| 4 | by oneself | N.D. | 2.54 | 0.01 | 4 | 8 |
| 5 | recognition | N.D. | 2.51 | 0.01 | 9 | 34 |
| 6 | happy | N.D. | 2.19 | 0.01 | 4 | 10 |
| 7 | interest | N.D. | 2.11 | 0.02 | 3 | 6 |
| 8 | husband | N.D. | 1.91 | 0.03 | 3 | 7 |
| 9 | improvement | N.D. | 1.88 | 0.03 | 2 | 3 |
| 10 | inside | N.D. | 1.88 | 0.03 | 2 | 3 |
| 11 | change | N.D. | 1.88 | 0.03 | 2 | 3 |
| 12 | human | N.D. | 1.74 | 0.04 | 3 | 8 |

N.D.: Not detected
*1 These words were used by the participants in the questionnaire before the lecture.

METHOD FOR ACHIEVING THE BALANCE OF THE MIND

BACKGROUND

Technical Field

The present invention relates to a method for achieving the balance of the mind of an examinee (a subject), and particularly relates to a method for achieving the balance of the mind of an examinee using a set of symbols.

Background Art

The number of people with mental disorder is recently increasing. In social life, it is becoming more difficult to maintain the balance of the mind. U.S. Pat. No. 5,213,562 discloses a measure for resolving mental problems by a method of inducing various states of consciousness by entraining brain waves into unique waveforms characteristic of specific states of consciousness by modulating the binaural beat signals with brain waves associated with particular activities.

SUMMARY

Technical Problem

The measure disclosed in U.S. Pat. No. 5,213,562 induces various states of consciousness by working on the examinee's auditory sense. In contrast, an object of the present invention is to provide a method for achieving the balance of the examinee's mind by using a set of symbols.

Solution to Problem

To achieve the above object, the present invention provides the methods shown in the following items.

Item 1.

A method for achieving the balance of the mind of an examinee, the method including a first step of showing a set of symbols to an examinee, a second step of applying the symbols to a feeling of the examinee and a state of the examinee's mind, a third step of making the examinee understand a recognition system represented by the set, and a fourth step of resolving a conflict in the examinee's mind to achieve the balance of the examinee's mind. The set includes a first symbol, a second symbol located obliquely below the first symbol, a third symbol that has a shape representing a concept in contrast with that of the second symbol, and that is a mirror image of the second symbol in terms of the position with respect to an imaginary vertical line passing through the first symbol, a fourth symbol that has a shape in common with that of the third symbol and that is located obliquely below the second symbol, and a fifth symbol that has a shape in common with that of the second symbol, and that is a mirror image of the fourth symbol in terms of the position with respect to an imaginary vertical line passing through the second symbol.

In the second step, the second symbol is associated with the examinee's thought, the third symbol is associated with an object of the examinee's thought (hereafter simply referred to as an "object"), the fourth symbol is associated with the examinee's unconsciousness, and the fifth symbol is associated with a blind spot in the examinee's mind. In the third step, the examinee is made to understand the recognition system by an explanation based on contrasting concepts between the second symbol and the third symbol, and between the fourth symbol and the fifth symbol, the explanation being that the blind spot in the examinee's mind associated with the fifth symbol represents a concept identified with by the examinee's thought associated with the second symbol and produces the examinee's unconsciousness associated with the fourth symbol, and that the feeling from the object associated with the third symbol is a projection of the examinee's unconsciousness associated with the fourth symbol. In the fourth step, the conflict in the examinee's mind is resolved by causing the examinee's unconsciousness and the blind spot in the examinee's mind to be exposed in the examinee's thought and pair-annihilated to achieve the balance of the examinee's mind.

Item 2.

The method further includes the second, fifth, and seventh symbols having a "+" shape, and the third, fourth, and sixth symbols having a "−" shape.

Item 3.

The method where the set further includes a sixth symbol that has a shape in common with that of the third symbol and that is located obliquely below the third symbol and a seventh symbol that has a shape in common with that of the second symbol, and that is a mirror image of the sixth symbol in terms of the position with respect to an imaginary vertical line passing through the third symbol. In the second step, the sixth symbol is associated with a blind spot in the object's mind, and the seventh symbol is associated with the object's unconsciousness. In the third step, the examinee is given an explanation that the blind spot in the object's mind associated with the sixth symbol represents a concept identified with by the object's thought associated with the third symbol and produces the object's unconsciousness associated with the seventh symbol, and that the feeling from the examinee associated with the second symbol is a projection of the object's unconsciousness associated with the seventh symbol.

Advantageous Effects of Invention

The present invention provides a method for achieving the balance of the mind of an examinee.

DETAILED DESCRIPTION

The following describes embodiments of the present invention with reference to accompanying drawings. However, the present invention is not limited to the following embodiments.

1. Set of Symbols

Figure 1:
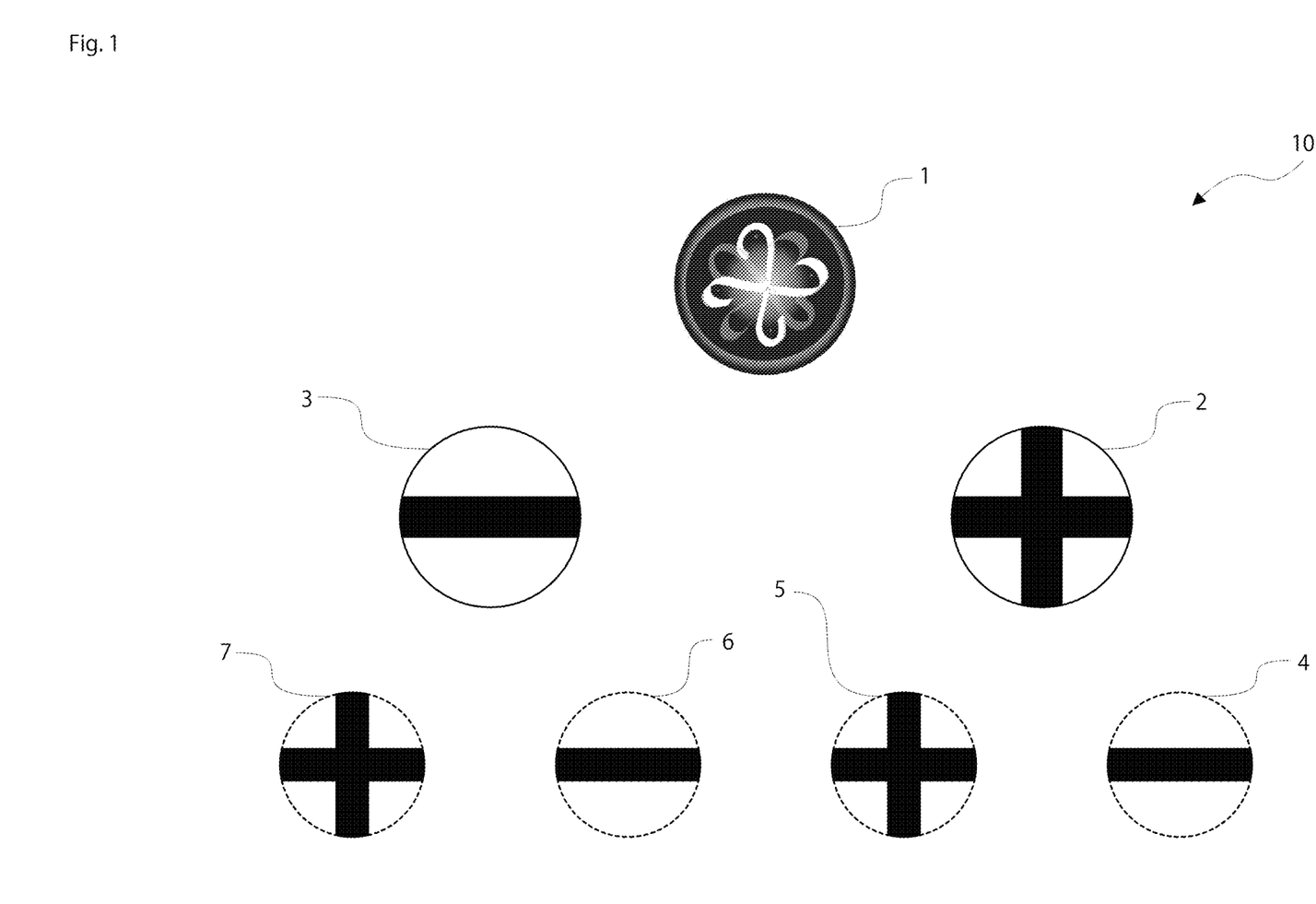
FIG. 1 is a set of symbols used in one embodiment of the present invention.

The present invention has a feature in that it uses a set of symbols to achieve the balance of the examinee's mind. FIG. 1 shows a set 10 of symbols (hereinafter referred to as a "set 10") used in one embodiment of the present invention.

The set 10 includes first to seventh symbols 1 to 7. The first to seventh symbols 1 to 7 are, as a whole, located in mirror-image positions. As described later, the set 10 is shown to an examinee on a display medium, such as a whiteboard, a Google Glass®, a paper medium, or a monitoring screen.

The first symbol 1 is located in the center of the uppermost of the set 10. The shape and pattern of the first symbol 1 are not particularly limited. However, the first symbol 1 does not have, at the very least, a shape or pattern that refers to an image biased to one of two contrasting concepts, such as "+" and "−."

The second symbol 2 is located obliquely below the first symbol 1. In this embodiment, the second symbol 2 is located obliquely to the right and downward from the first symbol 1 with a space therebetween, and has a "+" shape.

The third symbol 3 has a shape representing a concept in contrast with that of the second symbol 2, and is a mirror image of the second symbol 2 in terms of the position with respect to an imaginary vertical line passing through the first symbol 1. In this embodiment, the third symbol 3 has a "−" shape and is located obliquely to the left and downward from the first symbol 1 with a space therebetween.

The fourth symbol 4 has a shape in common with that of the third symbol 3, and is located obliquely below the second symbol 2. In this embodiment, the fourth symbol 4 has a "−" shape and is located obliquely to the right and downward from the second symbol 2 with a space therebetween.

The fifth symbol 5 has a shape in common with the second symbol 2, and is a mirror image of the fourth symbol 4 in terms of the position with respect to an imaginary vertical line passing through the second symbol 2. In this embodiment, the fifth symbol 5 has a "+" shape and is located obliquely to the left and downward from the second symbol 2 with a space therebetween.

The sixth symbol 6 has a shape in common with that of the third symbol 3, and is located obliquely below the third symbol 3. In this embodiment, the sixth symbol 6 has a "−" shape and is located obliquely to the right and downward from the third symbol 3 with a space therebetween.

The seventh symbol 7 has a shape in common with that of the second symbol 2, and is a mirror image of the sixth symbol 6 in terms of the position with respect to an imaginary vertical line passing through the third symbol 3. In this embodiment, the seventh symbol 7 has a "+" shape and is located obliquely to the left and downward from the third symbol 3 with a space therebetween.

As above, the shape of the second, fifth, and seventh symbols 2, 5, and 7 represents a concept in contrast with that of the shape of the third, fourth, and sixth symbols 3, 4, and 6. In this embodiment, the second, fifth, and seventh symbols 2, 5, and 7 have a "+" shape while the third, fourth, and sixth symbols 3, 4, and 6 have a "−" shape.

Figure 2:
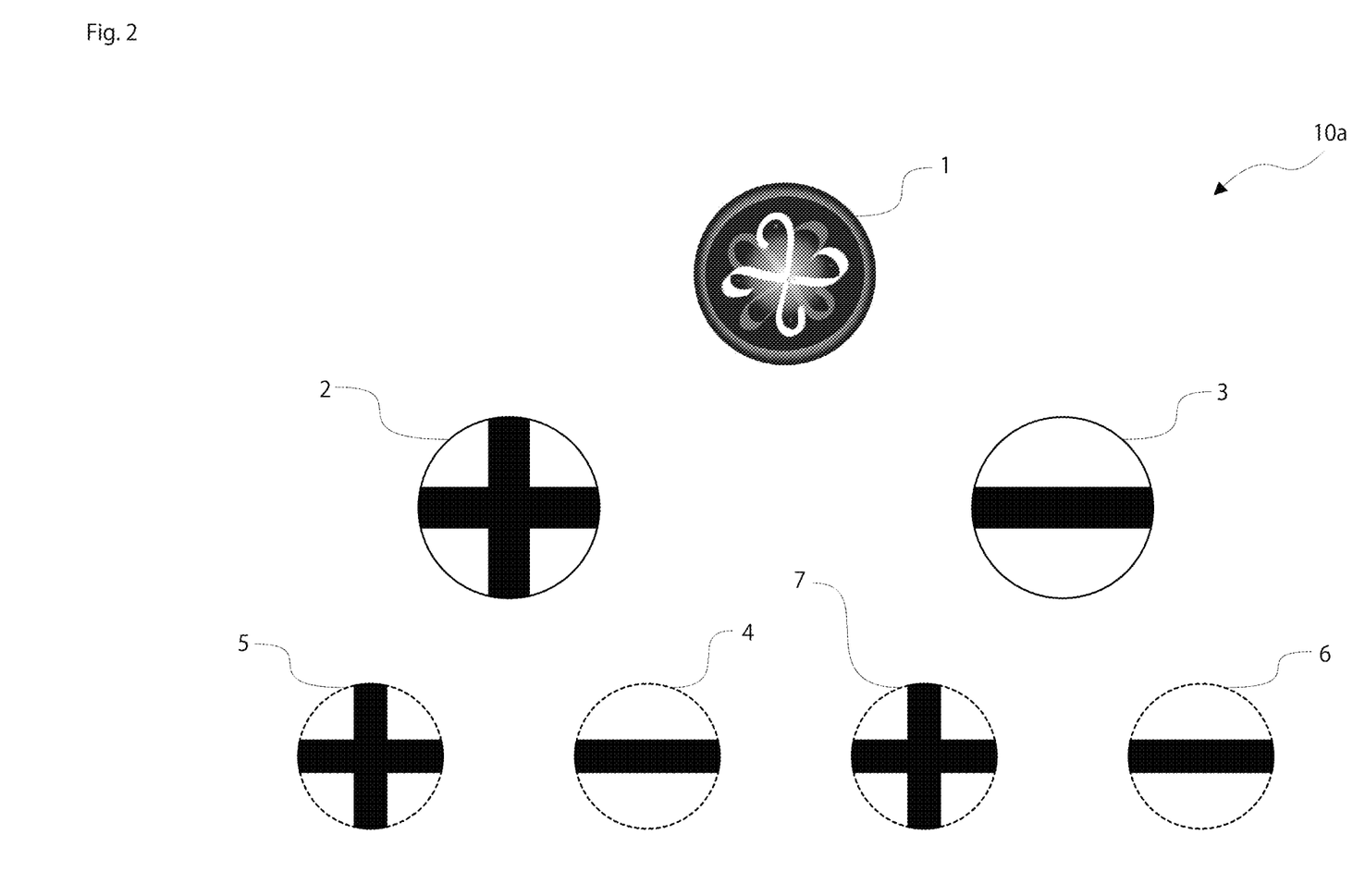
FIG. 2 is a modification of the above set.
Figure 3:
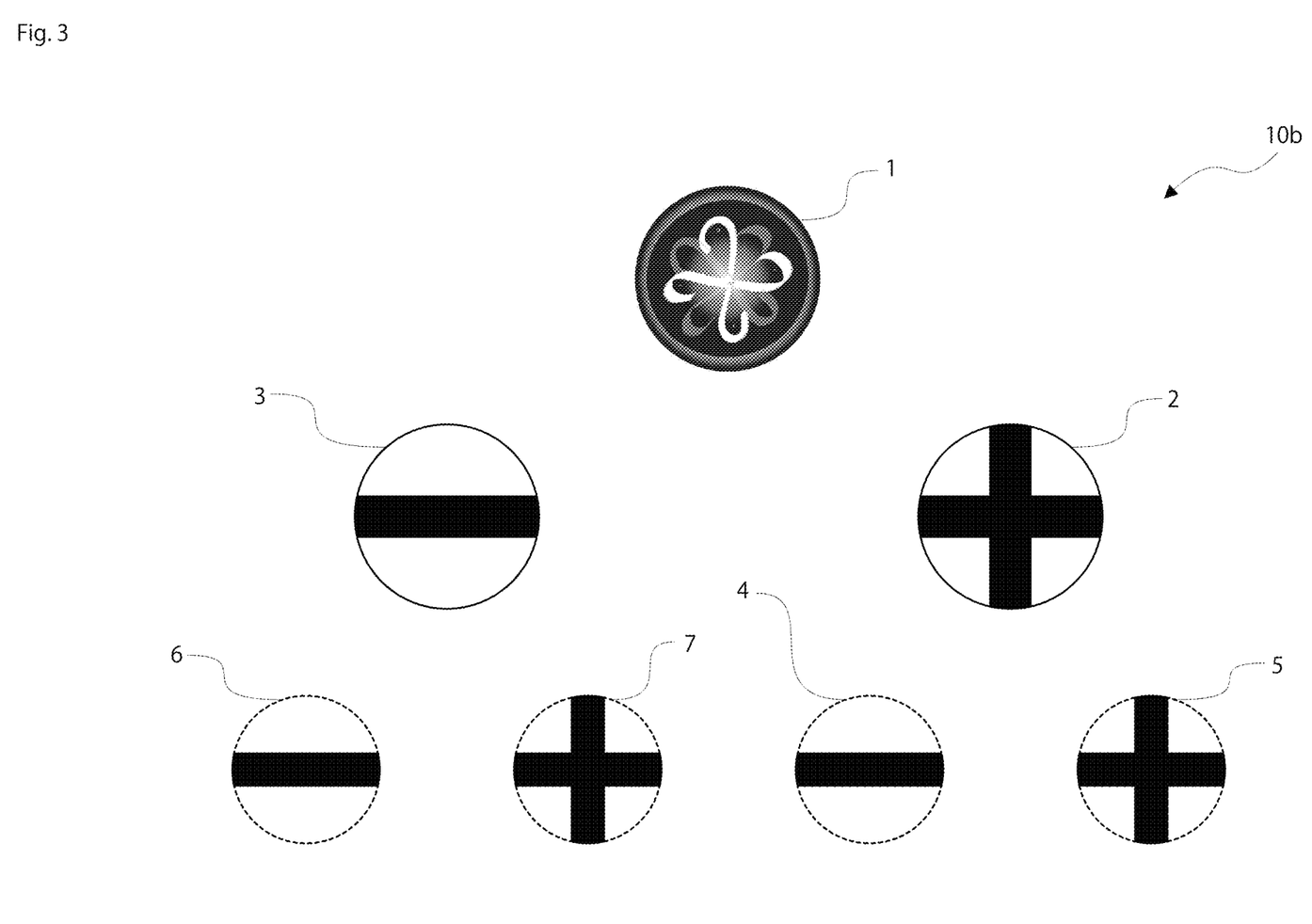
FIG. 3 is a modification of the above set.
Figure 4:
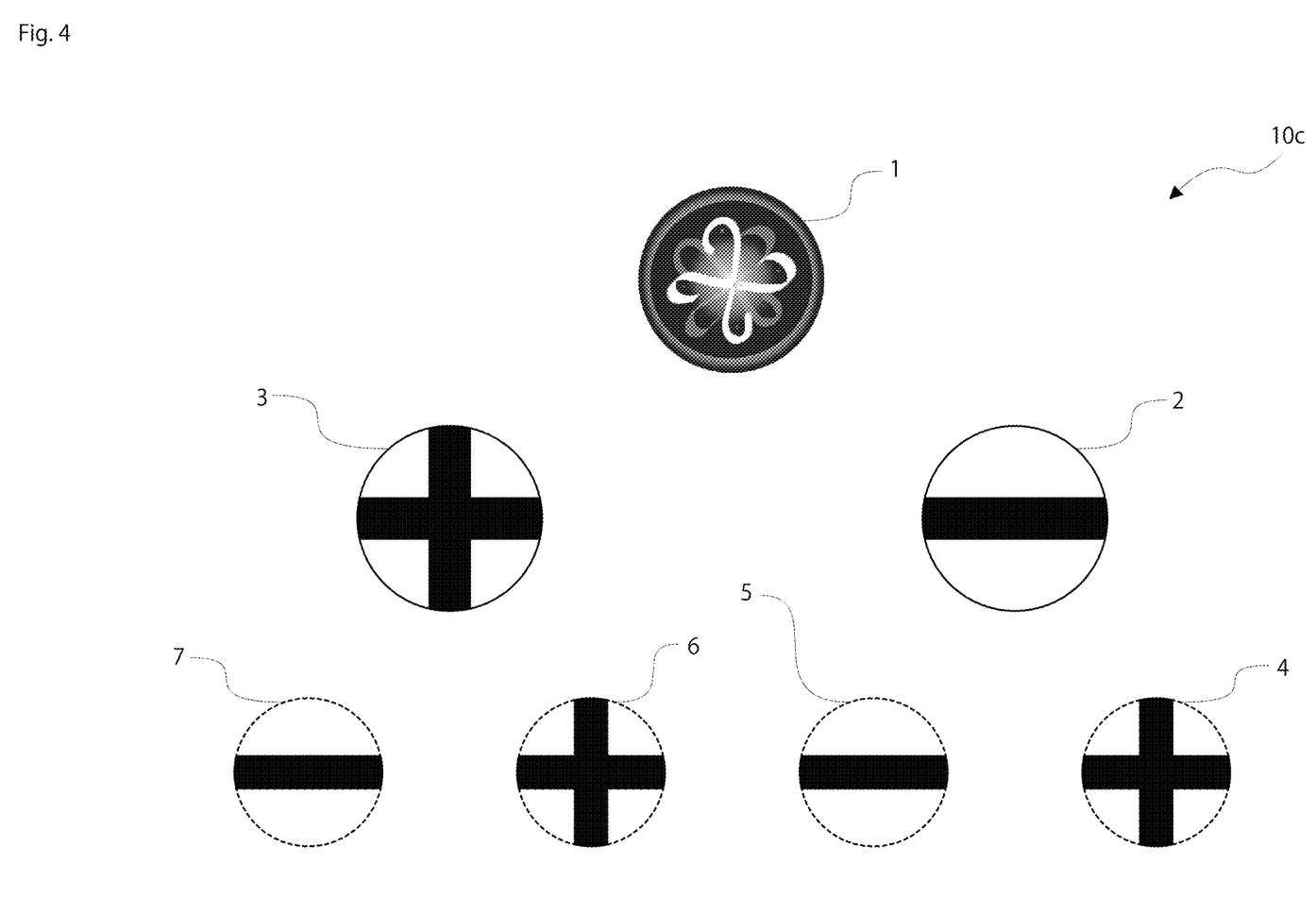
FIG. 4 is a modification of the above set.

The set used in the present invention is not limited to the set 10 shown in FIG. 1. FIGS. 2 to 4 show modifications of the set 10.

For example, the second symbol 2 and the third symbol 3 may be replaced with each other, as shown in the set 10a of FIG. 2. Further, in the set 10a, with the replacement between the second symbol 2 and the third symbol 3, the fourth and fifth symbols 4 and 5 and the sixth and seventh symbols 6 and 7 are replaced with each other.

In the set 10b shown in FIG. 3, the fourth symbol 4 and the fifth symbol 5 of the set 10 shown in FIG. 1 are replaced with each other while the sixth symbol 6 and the seventh symbol 7 are replaced with each other.

In the set 10c shown in FIG. 4, each of the second to seventh symbols 2 to 7 of the set 10 shown in FIG. 1 is made to have a shape representing the opposite concept. Specifically, in the set 10c, the second, fifth, and seventh symbols 2, 5, and 7 have a "−" shape while the third, fourth, and sixth symbols 3, 4, and 6 have a "+" shape.

In the second and third symbols 2 and 3, the "+" or "−" sign is surrounded by a solid-line circle. In the fourth to seventh symbols 4 to 7, the "+" or "−" sign is surrounded by a dotted-line circle. The solid line surrounding the second and third symbols 2 and 3 indicates that the second and third symbols 2 and 3 respectively correspond to the examinee's thought and an object of the examinee's thought. The dotted line surrounding the fourth to seventh symbols 4 to 7 indicates that these symbols correspond to a state of the examinee's mind that is not exposed. The "state of mind" specifically refers to the unconsciousness and blind spots in the mind of an examinee, as well as unconsciousness and blind spots in the mind of an object of the examinee's thought.

As described above, in the sets 10, 10a, 10b, and 10c according to the present invention, the first to seventh symbols 1 to 7, as a whole, are located bisymmetrically. Further, the second, fifth, and seventh symbols 2, 5, and 7 have a shape representing a concept in contrast with that of the third, fourth, and sixth symbols 3, 4, and 6.

In the examples shown in FIGS. 1 to 4, the second to seventh symbols 2 to 7 have a "+" or "−" shape. However, in the present invention, the shapes are not limited to these shapes as long as they represent concepts in contrast with each other. For example, "♂" and "♀," "O" and "X," "↑" and "↓" and "←" and "→" may be used. A pair of corresponding concepts may be applied to these contrasting shapes to implement the recognition system.

The shape or pattern of the first symbol 1 is different from those of the second to seventh symbols 2 to 7. The shape or pattern of the first symbol 1 is not particularly limited as long as it does not refer to an image biased to one of two contrasting concepts. In this embodiment, the first symbol 1 has a shape in which four pairs of Möbius strips are combined, representing a concept that is biased to neither "+" nor "−." The first symbol 1 may also be, for example, a white or black circle.

2. Procedure of Method

Figure 5:
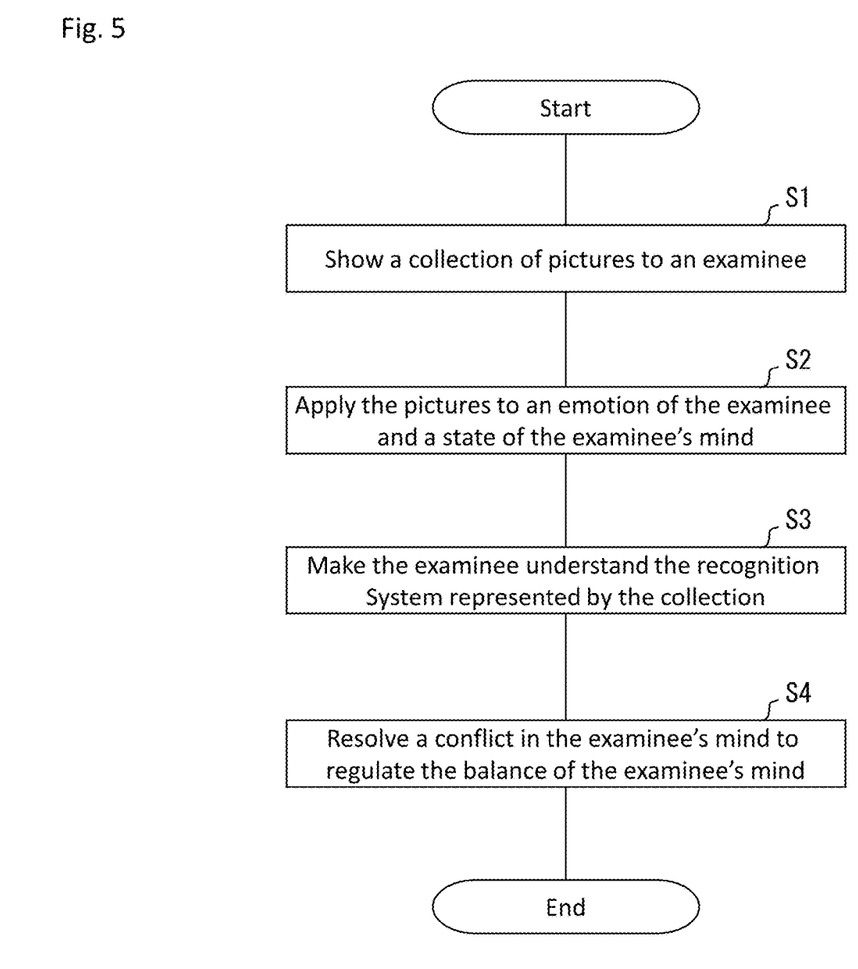
FIG. 5 is a flow chart showing the procedure of the method for achieving the balance of the mind according to one embodiment of the present invention.

FIG. 5 is a flow chart showing the procedure of the method for achieving the balance of the mind according to one embodiment of the present invention. The following describes the above method when performed in counseling style using the set 10 shown in FIG. 1.

In step S1, a counselor shows an examinee the set 10. The method of showing the set 10 is not particularly limited. For example, a paper medium on which the set 10 is described may be shown to an examinee, or a display medium, such as a whiteboard, a Google Glass®, a projector, a monitoring screen, or a tablet screen, may be used to display the set 10 and show it to an examinee.

Subsequently, in step S2, the counselor applies the symbols of the set 10 to an examinee's feeling and a state of the examinee's mind. Specifically, the second symbol 2 is associated with the examinee's thought, the third symbol 3 is associated with an object of the examinee's thought, the fourth symbol 4 is associated with the examinee's unconsciousness, the fifth symbol 5 is associated with a blind spot in the examinee's mind, the sixth symbol 6 is associated with a blind spot in the object's mind, and the seventh symbol 7 is associated with the object's unconsciousness. The "examinee's thought" as used herein does not refer to the entire thoughts of the examinee, and refers to a thought that produces conflicts in the mind of the examinee.

Figure 6:
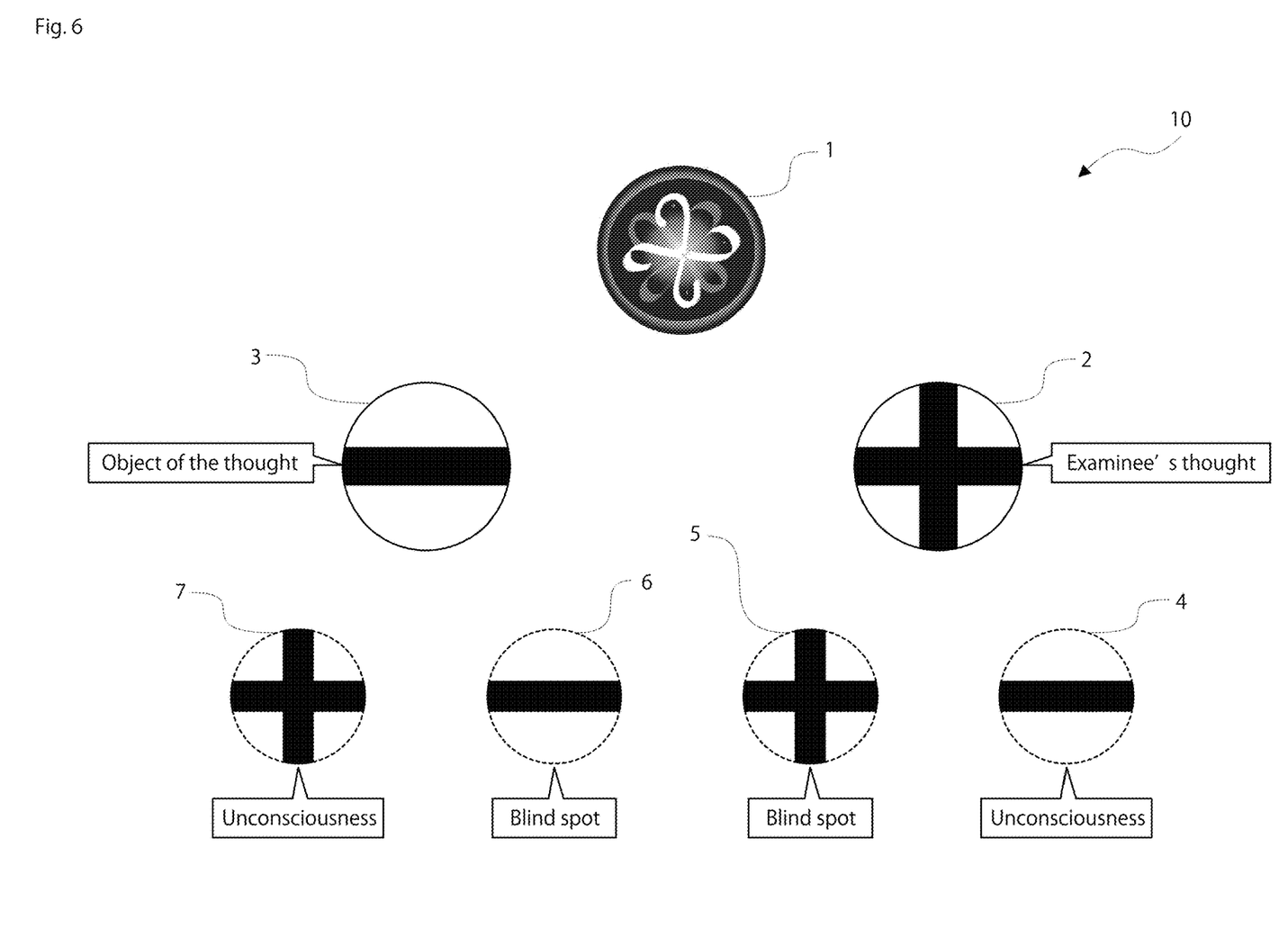
FIG. 6 shows speech balloons with concepts corresponding to each symbol of the set of FIG. 1.

The counselor may explain these associations to the examinee only in a verbal manner, or may show the concepts associated with each symbol using, for example, speech balloons on a monitoring screen or other display media, as shown in FIG. 6. Alternatively, when the set 10 is drawn on a whiteboard, a paper medium, or the like, the counselor may write by hand the concepts associated with each symbol. When the sixth and seventh symbols 6 and 7 are not included in the set 10, the association regarding the sixth and seventh symbols 6 and 7 is not performed.

Subsequently, in step S3, the examinee is made to understand the recognition system represented by the set 10, based on the contrasting concepts between the second symbol 2 and the third symbol 3, and between the fourth symbol 4 and the fifth symbol 5.

The second symbol 2 and third symbol 3 have different shapes representing concepts contrasting with each other. For example, as shown in FIGS. 1 to 3, when the second symbol 2 has a "+" shape, then the third symbol 3 has a "−" shape, and as shown in FIG. 4, when the second symbol 2 has a "−" shape, then the third symbol 3 has a "+" shape.

The shapes of "+" and "−" have a relation of opposite polarities. Likewise, the examinee's own thought and the examinee's feeling from an object have a relation of opposite polarities. For example, if the feeling from the object of the examinee's thought (hereinafter referred to as the "object") is assumed to be "coldness in a boss at a workplace," the feeling "coldness" is attributable to the examinee's thought, which is relatively "warm," compared to the boss. However, the examinee is not usually aware of this fact. Thus, in view of the recognition system represented by the set 10, the examinee's own feeling (warmth) that is recognized by the examinee's thought and the feeling (coldness) from the object of the examinee's thought are associated with the second symbol 2 and the third symbol 3, respectively. This allows the examinee to easily understand that the examinee's thought and the examinee's feeling from the object have opposite concepts, and allows the causes of conflicts in the mind, i.e., unconsciousness and a blind spot, to be exposed in the examinee's thought.

The counselor gives a questionnaire or the like to an examinee in advance to find out a specific cause of conflicts in the examinee's mind and the background of the examinee's life, and specifically explains to the examinee the meanings represented by the shapes of the symbols using expressions, such as "warmth (+)" and "coldness (−)." A pair of two concepts, i.e., a pair of two feelings and a pair of two states of mind, may be, for example, "independence" and "dependence," and "optimism" and "pessimism," in addition to "warmth" and "coldness."

The examinee's unconsciousness and a blind spot in the examinee's mind respectively associated with the fourth symbol 4 and the fifth symbol 5 are concepts with two polarities that produce conflicts in the examinee's mind. Everyone has these concepts in the mind. The unconsciousness and blind spot are in constant conflict in the mind, as in the fourth symbol 4 and the fifth symbol 5. In the example given above, when the examinee is feeling coldness in a boss at a workplace, there are concepts with two polarities inside the examinee's mind, i.e., "warmth (+)" and "coldness (−)," and the "warmth (+)" wins out over the conflict in the mind, allowing the examinee's thought (the second symbol 2) to identify with "warmth (+)." As a result, a phenomenon appears in which the examinee feels "coldness (−)" in the object of the examinee's thought. The "warmth (+)" is identified with by the examinee, which is why the examinee does not usually recognize their own "warmth" (blind spot=the fifth symbol 5). At the same time, the examinee's "coldness (−)" is below the consciousness, and the examinee cannot recognize that the coldness is the examinee's own state. The coldness is put into a state of unconsciousness (the fourth symbol 4). The "coldness" (the third symbol 3) that the examinee feels in a boss is the "coldness (−)" in the examinee in a state of unconsciousness projected onto the object in front of the examinee. Specifically, the feeling from the object (cold boss) of the thought recognized by the examinee is the examinee's own unconsciousness exposed to the examinee's thought.

As described above, a phenomenon in which the thought (+) identified with by the examinee (subject) is reversed and projected onto others (object: (−)) in front of the examinee is defined as a phenomenon of "reversal by identification." In the above example, the "warmth (+)" identified with by the examinee (subject) is reversed and projected as coldness (−) onto the boss before the examinee (object) who is an object of the examinee's thought.

As described above, the counselor explains to the examinee that the blind spot in the examinee's mind associated with the fifth symbol 5 represents a concept identified with by the examinee's thought associated with the second symbol 2, and at the same time, produces the examinee's unconsciousness associated with the fourth symbol 4, and that the object of the thought associated with the third symbol 3 is a projection of the examinee's unconsciousness associated with the fourth symbol 4. In the set 10, the third and fourth symbols 3 and 4 have a common shape, and the fifth symbol 5 has a shape representing a concept in contrast with that of the third and fourth symbols 3 and 4. Therefore, it is easy to understand the relationship between the symbols, based on their shapes, and thus to understand the recognition system represented by the set 10.

The counselor also explains to the examinee a case in which the examinee's thought (subject) and an object (object) of the examinee's thought are reversed. In this case, the counselor explains to the examinee that a blind spot in the object's mind associated with the sixth symbol 6 is identified with by the object's thought associated with the third symbol 3, and at the same time, produces the object's unconsciousness associated with the seventh symbol 7. Additionally, the counselor explains to the examinee that, the examinee's thought associated with the second symbol 2 is a projection of the object's unconsciousness associated with the seventh symbol 7, according to the phenomenon of "reversal by identification." Specifically, the counselor explains that unconsciousness and a blind spot also exist inside the mind of the object of the examinee's thought, similar to the inside of the examinee's mind as described above, although the polarities are different. When the set 10 does not include the sixth and seventh symbols 6 and 7, the description of this paragraph may be omitted.

The time required for performing the third step S3 is different for each individual. Some examinees may understand the recognition system with a single counseling session while others may require long-term counseling.

The fourth step S4 resolves conflicts in the examinee's mind to achieve the balance of the mind. Specifically, the unconsciousness and blind spot in the examinee's mind are exposed in the examinee's thought. Unconsciousness and a blind spot in the mind are not both recognized by the examinee; however, in the third step S3, when the examinee understands that the unconsciousness of the examinee is projected onto the object of the examinee's thought before the examinee, based on the phenomenon "reversal by identification," the examinee recognizes the unconsciousness present in the examinee's own mind and allows it to be exposed.

In other words, the direction of the examinee's thought toward the object (the third symbol 3) is reversed so that the examinee's thought is directed to the examinee's own unconsciousness (the fourth symbol 4). For example, when the "coldness in a boss" is considered as the feeling from the object of the examinee's thought, the "coldness in a boss" is the coldness in the examinee's unconsciousness projected onto the boss. When the direction of the thought regarding the feeling of coldness is reversed toward the examinee him/herself, the examinee's unconsciousness (coldness) is allowed to be exposed in the examinee's thought. Along with this, the examinee also recognizes the "warmth," i.e., a blind spot in the mind, which is identified with by the examinee him/herself. This is specifically a state in which the blind spot in the examinee's mind is exposed in the thought.

When the examinee's unconsciousness (the fourth symbol 4) and the blind spot in the examinee's mind (the fifth symbol 5) are exposed in the examinee's thought, they fuse with each other as in the positive and negative charges of electrical energy, and are pair-annihilated. As a result, the thought associated with the second symbol 2 that caused a conflict in the examinee's mind also disappears. The first symbol 1 is located at the top of the set 10, which includes bisymmetrically positioned first to seventh symbols 1 to 7. The first symbol 1 has a shape or pattern that is not biased to one of "+" and "−." Specifically, the first symbol 1 indicates that the examinee's thought (the second symbol 2) biased toward "+" disappears, and the examinee's viewpoint is shifted from the second symbol 2 to a position (the first symbol 1) overviewing the entire recognition system represented by the set 10. Thus, when the counselor makes the examinee understand that the fourth symbol 4 (−) and the fifth symbol 5 (+) are pair-annihilated, and that the examinee's viewpoint is shifted from the second symbol 2 to the first symbol 1, the examinee's unconsciousness and the blind spot in the examinee's mind are easily pair-annihilated. Specifically, the first symbol 1 shows a balanced state of mind with no judgment of whether it is cold or not cold, or whether it is warm or not warm. More specifically, the first symbol 1 overviews the second and third symbols 2 and 3 simultaneously, and further overviews the second to seventh symbols 2 to 7, as well. That is, the first symbol 1 represents a state of the examinee who gained a new viewpoint and becomes relaxed, being free from the two polarities of "approval (+)" and "denial (−)," i.e., (+) and (−), in the mind.

When the examinee's unconsciousness (the fourth symbol 4) disappears, a projection of the examinee's unconsciousness, i.e., the feeling from the object of the examinee's thought (the third symbol 3), also disappears at the same time. As a result, the balance of the mind of the examinee is achieved.

For example, the "coldness in a boss" is assumed to be a feeling from the object of the thought. In this case, when the conflict in mind is dissolved, the examinee no longer feels coldness in the boss, and no longer experiences stress from the boss.

The same applies to a case in which the subject and the object are reversed. Specifically, when the thought that causes a conflict in the examinee's mind and that is associated with the second symbol 2 disappears, the third symbol 3, which is an object of the examinee's thought also disappears at the same time. At this time, the unconsciousness in the mind associated with the seventh symbol 7 also disappears, and along with this, the blind spot associated with the sixth symbol 6 also disappears.

When the sixth and seventh symbols 6 and 7 are respectively associated with a blind spot and unconsciousness of the object of the examinee's thought, the examinee furthermore easily understands the recognition system represented by the set 10.

3. Others

An embodiment of the present invention is described above. However, the present invention is not limited to the above embodiment, and various modifications may be made without departing from the spirit of the present invention.

In the above embodiment, the method of the present invention is performed in one-to-one counseling style. The method may also be performed, for example, in lecture style or in non-face-to-face lecture style by using a communication medium, such as the Internet. In addition to a counselor, a subject that implements the method of the present invention to achieve the balance of the mind of an examinee may be a computer, a robot, or artificial intelligence that is programmed to perform the procedures of steps S1 to S4 described in this specification. Such a computer or the like may be provided with a cloud. Alternatively, the examinee may personally practice the method by using an instructional material (a paper medium or application executed on a computer) for performing the method.

The method of the present invention is for achieving the balance of the examinee's mind by completing specific procedures using a set of symbols. The target of this method does not involve natural laws, natural phenomenon, or abstract ideas.

The above embodiment is an example in which the object of the examinee's thought is a boss of the examinee; however, the object of the examinee's thought is not limited thereto. The object of the thought is not particularly limited and may be a parent, spouse, friend, son, etc., of the examinee as long as they are a cause of a conflict in the examinee's mind.

3-1. Modification 1

Furthermore, the object of the examinee's thought is not necessarily a person. For example, when an examinee feels "unreasonableness" against a community to which the examinee belongs, the "community" serves as the object of the thought of the examinee. The following describes an example in which the method of the present invention is applied to such an examinee in counseling style, based on FIG. 5.

First, in step S1, a counselor shows an examinee a set 10. Then, in step S2, the counselor applies the symbols of the set 10 to an examinee's feeling and a state of the examinee's mind. Steps S1 and S2 are the same as the steps used in the embodiment described above.

Subsequently, in step S3, the counselor makes the examinee understand the recognition system represented by the set 10, based on the contrasting concepts between the second symbol 2 and the third symbol 3, and between the fourth symbol 4 and the fifth symbol 5. Specifically, the counselor explains the following matters to the examinee.

The examinee's mind contains concepts with two polarities, such as "justice (+)" and "unreasonableness (−)," which produce a conflict. In the conflict, the "justice" wins out over the "unreasonableness," and the examinee's thought (the second symbol 2) identifies with the "justice." Thus, the examinee is not usually aware of the "justice" inside his/her mind, and the "justice" serves as a blind spot associated with the fifth symbol 5. At the same time, the "unreasonableness" in the mind of the examinee is below the examinee's consciousness; thus, the examinee does not recognize that the "unreasonableness" is the examinee's own state, and the "unreasonableness" is put into a state of unconsciousness associated with the fourth symbol 4. The examinee's "unreasonableness" feeling against the community (the third symbol 3) is the "unreasonableness" in the examinee in the state of unconsciousness and is projected onto the object of the examinee's thought. Specifically, the "justice" that is identified with by the examinee is projected onto the object of the examinee's thought as "unreasonableness," based on the phenomenon of "reversal by identification."

When the examinee understands the recognition system represented by the set 10 with the above explanation, the step is advanced to step S4. The counselor then causes the examinee's unconsciousness and a blind spot in the examinee's mind to be exposed in the examinee's thought. Specifically, the examinee reverses the direction of the thought regarding the "unreasonableness" feeling against the community, so that it is directed toward the examinee him/herself. The examinee then becomes aware of his/her own unconsciousness (unreasonableness), and the unconsciousness becomes exposed in the thought. Along with this, the examinee recognizes the "justice," which is a blind spot in mind identified with by the examinee him/herself, and the blind spot in the examinee's mind is also exposed in the examinee's thought.

In this manner, the examinee's unconsciousness (the fourth symbol 4) and the blind spot in the examinee's mind (the fifth symbol 5) are pair-annihilated, and as a result, the thought that causes a conflict in the examinee's mind associated with the second symbol 2 also disappears. At the same time, the feeling from the object of the examinee's thought, i.e., a projection of the examinee's unconsciousness (the third symbol 3), also disappears. It is thereby possible for the examinee to achieve the balance of the mind. The examinee thus no longer feels unreasonableness against the community.

3-2. Modification 2

In another embodiment, the method according to the present invention is applied to an examinee having a sense of inferiority to others in counseling style as described below.

First, in step S1, a counselor shows an examinee a set 10. Then, in step S2, the counselor applies the symbols of the set 10 to an examinee's feeling and a state of the examinee's mind. The steps S1 and S2 are the same as the steps used in the embodiment described above.

Subsequently, in step S3, the counselor makes the examinee understand the recognition system represented by the set 10, based on the contrasting concepts between the second symbol 2 and the third symbol 3, and between the fourth symbol 4 and the fifth symbol 5. Specifically, the counselor explains the following matters to the examinee.

The examinee's mind contains concepts with two polarities, such as "sense of superiority (+)" and "sense of inferiority (−)," which produce a conflict. In the conflict, the "sense of superiority" wins out over the "sense of inferiority," and the examinee's thought (the second symbol 2) identifies with the "sense of superiority." Thus, the examinee is not usually aware of the "sense of superiority" inside his/her mind, and the "sense of superiority" serves as a blind spot associated with the fifth symbol 5. At the same time, the examinee's "sense of inferiority" is below the consciousness; thus, the examinee does not recognize that the "sense of inferiority" is the examinee's own state, and the "sense of inferiority" is put into a state of unconsciousness associated with the fourth symbol 4. The examinee's "sense of inferiority" feeling from the object (the third symbol 3) of the examinee's thought is the "sense of inferiority" in the examinee's unconsciousness projected onto the object of the examinee's thought.

When the examinee understands the recognition system represented by the set 10 with the above explanation, the step is advanced to step S4. The counselor then causes the examinee's unconsciousness and a blind spot in the examinee's mind to be exposed in the examinee's thought. Specifically, the examinee reverses the direction of the thought regarding the "sense of inferiority" feeling from the object of the examinee's thought, so that it is directed to the examinee him/herself. The examinee then becomes aware of his/her own unconsciousness, and the unconsciousness becomes exposed in the thought. Along with this, the examinee recognizes the "sense of superiority," which is a blind spot in mind identified with by the examinee him/herself, and the blind spot in the examinee's mind is also exposed in the examinee's thought.

In this manner, the examinee's unconsciousness (the fourth symbol 4) and the blind spot in the examinee's mind (the fifth symbol 5) are pair-annihilated, and as a result, the thought that causes conflicts in the examinee's mind associated with the second symbol 2 also disappears. At the same time, the feeling from the object of the examinee's thought, i.e., a projection of the examinee's unconsciousness (the third symbol 3), also disappears. It is thereby possible for the examinee to achieve the balance of the mind. The examinee no longer has a sense of inferiority to others.

Examples

The following are Examples of the present invention. However, the present invention is not limited to these Examples.

In the Example, the method of the present invention using a set 10 was performed in lecture style. The data shown in FIGS. 7 to 9 were compiled by studying questionnaires from a randomly selected 10 percent (31 participants) of the 317 participants. The participants were suggested to freely write down their mental experience before and after their participation.

Questions

Before the participation: What is the motivation, purpose, or reason that made you participate in the lecture?

After the participation: What do you feel now?

First, using text mining techniques, spaces were added between the words in the sentences that the participants provided in the questionnaires before and after the lecture, and then, lists of the top 12 characteristic keywords that participants used before and after their participation were compiled. Word Miner (registered trademark, Japan Information Processing Service Co., Ltd.) was used to process the data. The number of effective samples was 31.

Figure 7:
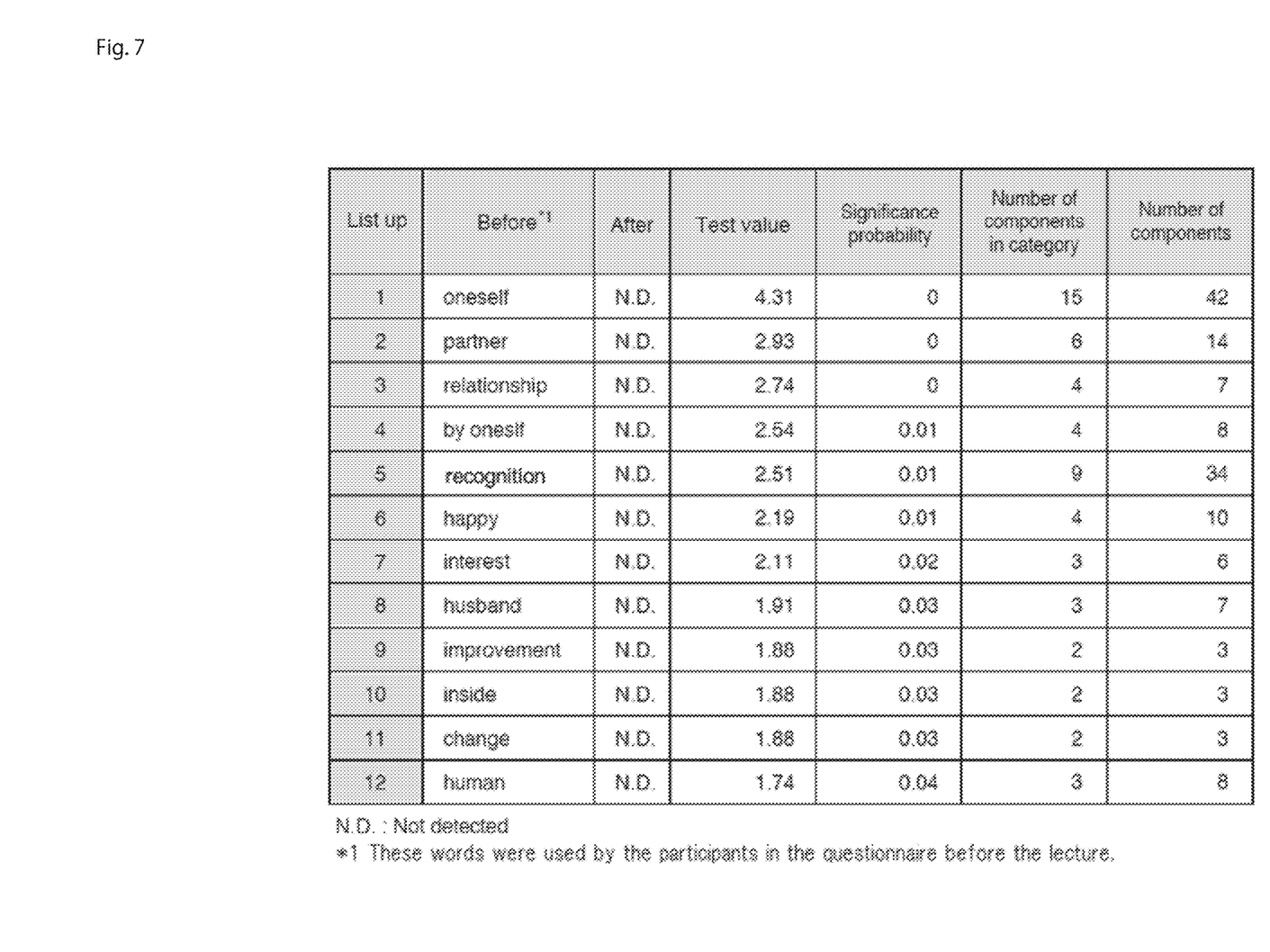
FIG. 7 shows data compiled based on questionnaires from participants of the lecture according to the method of the present invention in the Example.

As shown in Table 7, while the participants wrote down such words from their unconsciousness as "oneself," "partner," and "relationship" in their answers of the question (the motivation, purpose, or reason) before the participation, those words were statistically never used after the lecture. It became statistically clear that the frequency with which such words were unconsciously used by the participants decreased dramatically due to the change in their sensations, i.e., pair-annihilation of unconsciousness and a blind spot.

In addition, a statistical test value (a test value based on hypergeometric distribution) and significance probability were determined. The table in FIG. 7 indicates the statistically significant probability (Significance Probability <0.05), which is less probable than the statistical significance standard of 5%.

This result was not obtained by accident. From the perspective of mathematical statistics, this peculiar phenomenon is considered to have inevitably occurred, in view of the hypothesis (rejection of the null hypothesis=adoption of the alternate hypothesis) that the unconsciousness and a blind spot are pair-annihilated in this statistical parent population.

Figure 8:
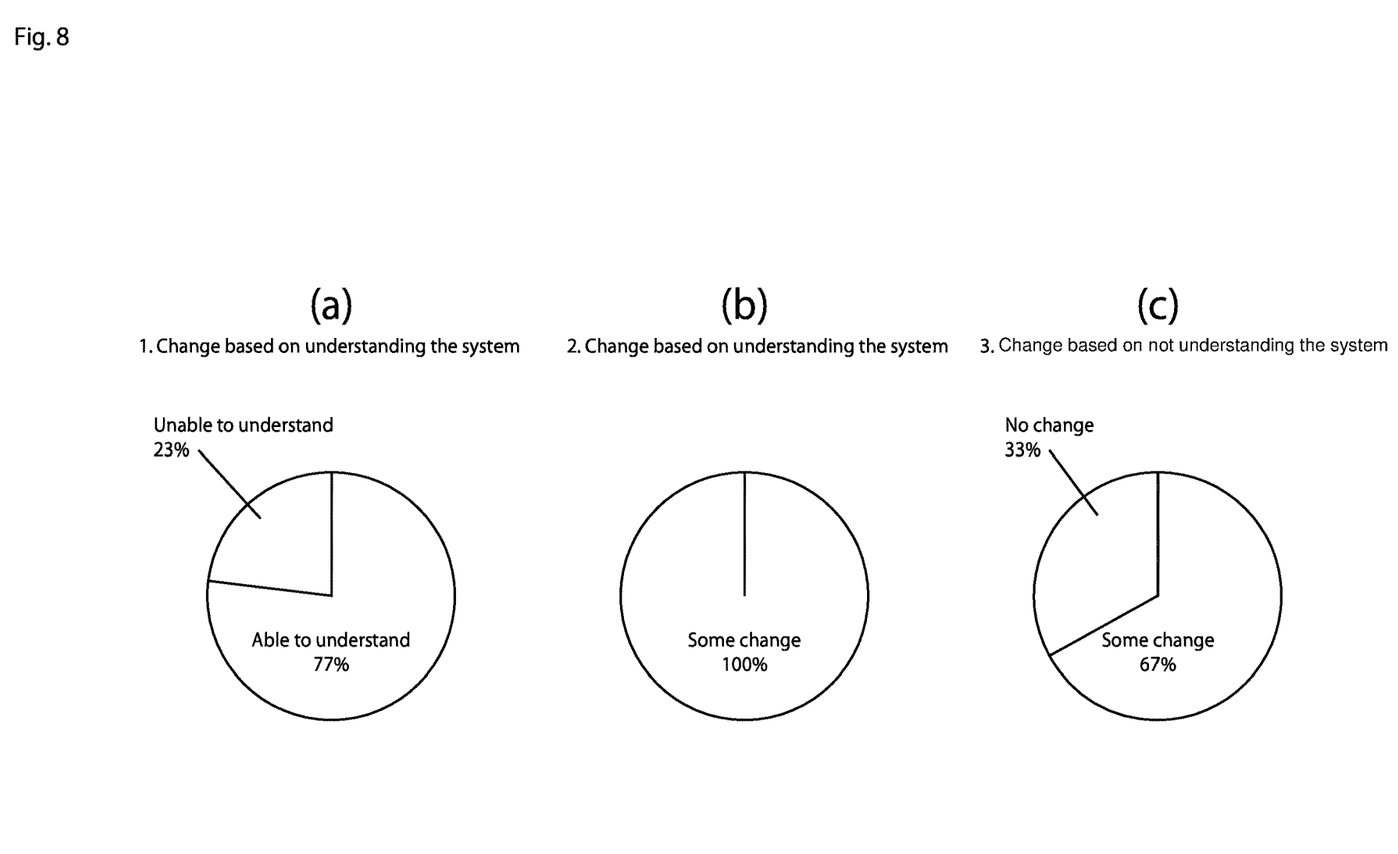
FIG. 8 shows graphs that indicate changes in participants before and after the attendance of the lecture according to the method of the present invention in the Example.

Next, FIGS. 8(a) to (c) present the changes in the participants before and after the method of the present invention was conducted.

(a) Did you understand the recognition system represented by the set 10?
Yes: 77%, No: 23%
(b) If the answer was "Yes" to question (a), have you experienced any change?
Yes: 100%
(c) If the answer was "No" to question (a), have you experienced any change?
Yes: 67%, No: 33%

As shown in FIG. 8(b), all of the participants who answered that they had understood the recognition system represented by the set 10 felt that they had experienced changes in terms of their purposes after participating in the lecture. After understanding the recognition system represented by the set 10, the participants at the very least recognized concepts having two polarities in their mind associated with the fourth and fifth symbols 4 and 5, and the concepts having two polarities are thus caused to be exposed in their thought. Then, the unconsciousness and blind spot disappeared, allowing the balance of the mind to be achieved. As a result, the participants whose conflict in mind had disappeared saw a phenomenon that reflected the state in which the balance of the mind was achieved.

Of the 23% of participants who answered that they had not been unable to understand, 67% experienced a change (FIG. 8(c)). The participants who were unable to understand the recognition system represented by the set 10 still experienced some changes. This means that the present invention enables the acquisition of new viewpoints for overviewing the entire recognition system, allowing the balance of the mind to be achieved. There seems to be a discrepancy in the results that the participants who did not understand the recognition system represented by the set 10 still experienced a change. However, in light of the phenomenon of "reversal by identification" of the recognition system represented by the set 10, the thought itself of the participant who did not understand the system represents a blind spot (unable to understand) of the participant, and at the same time, the participant's unconsciousness (wish to understand the system) produced the counselor (who understands the system) before the participant. Then, as a result of the reversal, the participant answered the questions, referring to the phenomenon in which he or she was unable to understand the system in terms of their thought.

Meanwhile, 33% of the participants answered that they had not understood the recognition system represented by the set 10 and that there had not been any changes. However, all of these participants still experienced some changes regarding their purpose of participation after participating in the follow-up lectures.

The participants who did not perceive any changes before participating in the follow-up lecture (33%, FIG. 8(c)) were assumed to try to understand the recognition system represented by the set 10 by applying it to the framework of conventional thought patterns. Unlike the first symbol 1, the conventional thought patterns involve no viewpoint that overviews the entire recognition system, and it is thus difficult for them to achieve the balance of the mind.

However, the participants who did not experience any change (33%, FIG. 8(c)) later experienced some change after understanding the recognition system represented by the set 10 at the follow-up lectures. This means that the balance of their mind was achieved. These results suggest that the more frequently the method of the present invention using the set 10 is performed, the more likely change is to occur.

Figure 9:
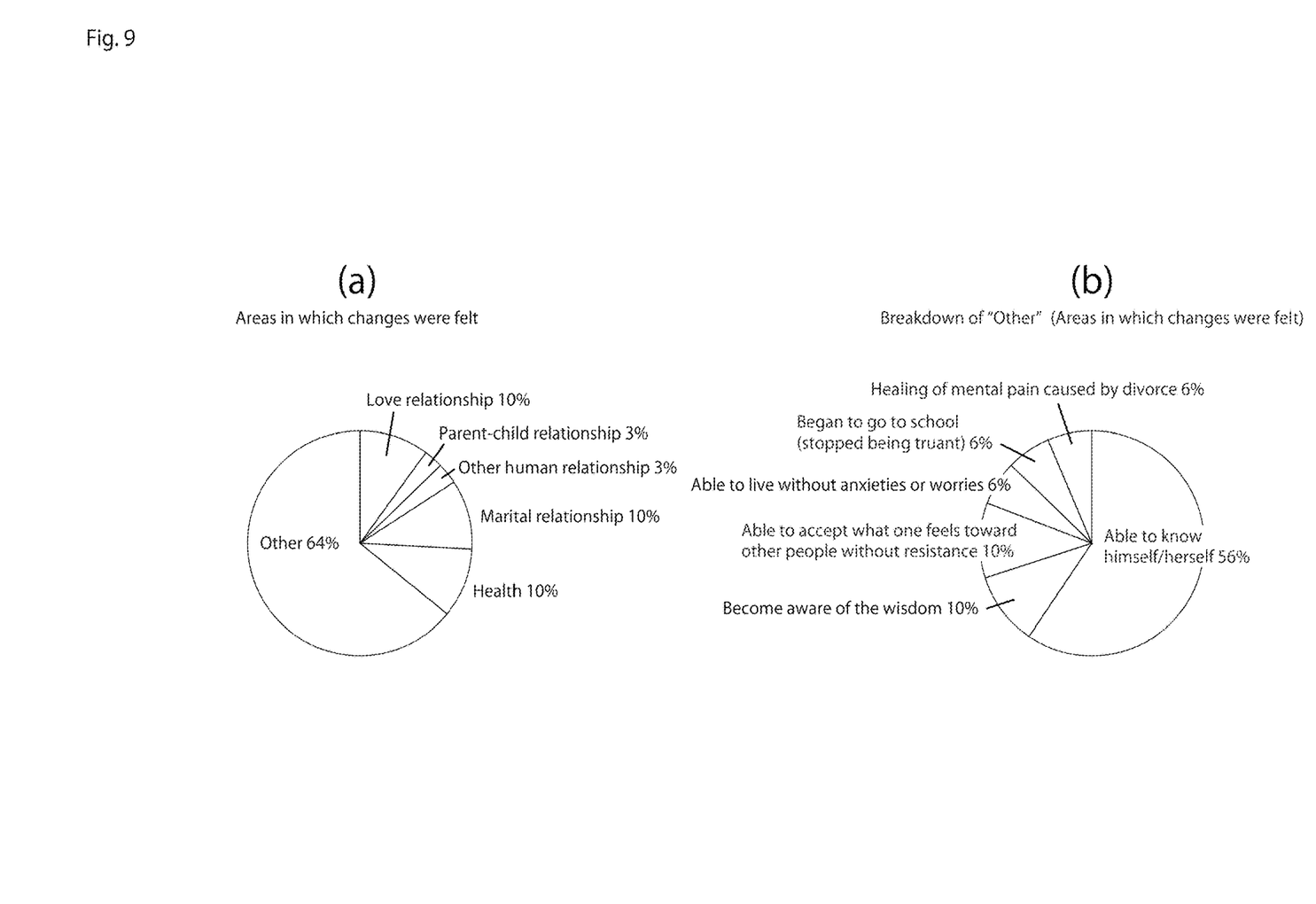
FIG. 9 shows graphs that indicate areas in which the participants of the lecture according to the method of the present invention in the Example felt change.

FIGS. 9(a) and (b) show the areas in which the participants felt change. FIG. 9(a) shows the answers to the question: In what area did you experience any change after understanding the recognition system?
Love relationship: 10%
Marital relationship: 10%
Health: 10%
Parent-child relationship: 3%
Other human relationship: 3%
Other: 64%

FIG. 9(b) shows a breakdown of those who answered "Other" in FIG. 9(a).
Able to know himself/herself: 56%
Become aware of the wisdom: 10%
Able to accept what one feels toward other people without resistance: 10%
Able to live without anxieties or worries: 6%
Began to go to school (stopped being truant): 6%
Healing of mental pain caused by divorce: 6%

These results indicate that the acquisition of new viewpoints achieved the balance (inside) of the mind of the participants, and thus it became possible for the participants to live without feeling conflicts in everyday life (outside). These results also indicate that an internal change in the viewpoints of the examinee had an influence on the external environment.

INDUSTRIAL APPLICABILITY

The present invention is suitably applied to fields in which problems in human relationships (e.g., communication, love, marriage, and child-raising) are solved, and is also applied to fields of psychological medical treatment.

EXPLANATION OF REFERENCE NUMERALS

First symbol 1
Second symbol 2

Third symbol 3
Fourth symbol 4
Fifth symbol 5
Sixth symbol 6
Seventh symbol 7
Set of symbols 10
Set of symbols 10a
Set of symbols 10b
Set of symbols 10c

What is claimed is:

1. A method for achieving a balance of mind of an examinee, the method comprising:

providing a plurality of questions from a questionnaire for an examinee to answer, wherein the questionnaire is configured to obtain information about conflict in the examinee's mind and background of the examinee's life;

showing a set of symbols, on a display, to the examinee, wherein:
the set of symbols comprises a first symbol, a second symbol, a third symbol, a fourth symbol, and a fifth symbol;
the first symbol positioned at a top center position;
the second symbol positioned below and to a first side of the first symbol;
the third symbol positioned symmetrically across from the second symbol, below and to a second side of the first symbol;
the fourth symbol positioned below and to a first side of the second symbol;
the fifth symbol positioned symmetrically across from the fourth symbol, below and to a second side of the second symbol;
the second symbol and the fifth symbol having a first shape in common; and
the third symbol and the fourth symbol having a second shape in common, the second shape being in contrast from the first shape;

explaining to the examinee a recognition system that comprises the set of symbols, wherein:
the second symbol is explained to be a thought that produces a conflict in the examinee, as indicated by one or more responses to the plurality of questions from the questionnaire;
the third symbol is explained to be an object of the thought that produces the conflict; and
the fourth and fifth symbols are explained to be a pair of opposing concepts that produce the conflict in the examinee, wherein:
the fifth symbol is explained to be a first concept of the pair, the first concept relating to the second symbol, wherein the fifth symbol is a blindspot in the examinee's mind; and
the fourth symbol is explained to be a second concept of the pair, the second concept relating to the third symbol, wherein the fourth symbol is the examinee's unconsciousness;

describing to the examinee the recognition system for understanding a relationship between the symbols and the concepts based on the contrasting shapes and symmetrical positioning of the symbols, wherein the recognition system of the examinee is based on responses to the questions from the questionnaire;

resolving the conflict of the examinee by directing the opposing second concept from the third symbol to the fourth symbol; and providing a second questionnaire that is used in an analysis to measure treatment efficacy.

2. The method according to claim 1, wherein;
the second symbol and the fifth symbol have a "+" shape; and
the third symbol and the fourth symbol have a "−" shape.

3. The method according to claim 1, wherein the set of symbols further comprises a sixth symbol and a seventh symbol;
the sixth symbol positioned below and to a first side of the third symbol;
the seventh symbol positioned symmetrically across from the sixth symbol, below and to a second side of the third symbol;
the sixth symbol having the second shape in common with the third symbol and the fourth symbol; and
the seventh symbol having the first shape in common with the second symbol and the fifth symbol.

4. The method according to claim 3, wherein:
the sixth symbol is explained to be a third concept, the third concept relating to the third symbol; and
the seventh symbol is explained to be a fourth concept, the fourth concept relating to the second symbol.

5. The method according to claim 3, wherein:
the sixth symbol has a "−" shape; and
the seventh symbol has a "+" shape.

6. A method for achieving a balance of mind of an examinee, the method comprising:

providing a plurality of questions from a questionnaire for an examinee to answer, wherein the questionnaire is configured to obtain information about conflict in the examinee's mind and background of the examinee's life;

showing a set of symbols, on a display, to the examinee, the set of symbols comprising a first symbol, a second symbol, a third symbol, a fourth symbol, and a fifth symbol, the first symbol having a first shape, the second and the fifth symbols having a second shape in common, and the third and the fourth symbol having a third shape in common, the second and third shapes in contrast with one another;

the first symbol positioned at a top center position, the second symbol positioned below and to one side of the first symbol, the third symbol is positioned below the first symbol and symmetrically across from the second symbol relative to an imaginary vertical line passing through the first symbol, the fourth symbol positioned below and to one side of the second symbol, and the fifth symbol positioned below the second symbol and symmetrically across from the fourth symbol relative to an imaginary vertical line passing through the second symbol;

explaining a recognition system comprising the set of symbols, wherein the second symbol is explained to be a thought that produces a conflict in the examinee based on one or more responses to the plurality of questions from the questionnaire, the third symbol is explained to be an object of the thought that produces the conflict, the fourth symbol is explained to be an unconscious state of mind of the examinee, and the fifth symbol is explained to be a blind spot in the examinee's mind;

describing to the examinee the recognition system for understanding a relationship between the symbols based on the contrasting shapes and symmetrical positions of the symbols, wherein the recognition system of the examinee is based on responses to the questions from the questionnaire;

resolving the conflict of the examinee by exposing the unconscious state of mind and the blind spot corresponding with the fourth and fifth symbols; and providing a second questionnaire that is used in an analysis to measure treatment efficacy.

7. The method according to claim 6, wherein;
the second symbol and the fifth symbol have a "+" shape; and
the third symbol and the fourth symbol have a "−" shape.

8. The method according to claim 6, wherein exposing the unconscious state of mind and the blind spot comprises:
identifying a first concept from the second symbol having the second shape with the blind spot in the examinee's mind corresponding with the fifth symbol, and
identifying a second concept from the third symbol having the third shape with the unconscious state of mind of the examinee corresponding with the fourth symbol, the first and second concepts in contrast with one another.

9. The method according to claim 6, wherein the set further comprises a sixth symbol and a seventh symbol;
the sixth symbol positioned below and to one side of the third symbol;
the seventh symbol positioned below the third symbol and symmetrically across from the sixth symbol relative to an imaginary vertical line passing through the third symbol;
the sixth symbol having the third shape in common with the third symbol and the fourth symbol; and
the seventh symbol having the second shape in common with the second symbol and the fifth symbol.

10. The method according to claim 9, wherein:
the sixth symbol has a "−" shape; and
the seventh symbol has a "+" shape.

11. A system for achieving a balance of mind of an examinee, the system comprising:
a computer configured to provide a plurality of questions from a questionnaire for an examinee to answer, wherein the questionnaire is configured to obtain information about conflict in the examinee's mind and background of the examinee's life; and
a display associated with the computer, the display displaying of a set of symbols, wherein:
the set of symbols comprises a first symbol, a second symbol, a third symbol, a fourth symbol, and a fifth symbol;
the first symbol positioned at a top center position;
the second symbol positioned below and to a first side of the first symbol;
the third symbol positioned symmetrically across from the second symbol, below and to a second side of the first symbol;
the fourth symbol positioned below and to a first side of the second symbol;
the fifth symbol positioned symmetrically across from the fourth symbol, below and to a second side of the second symbol;
the second symbol and the fifth symbol having a first shape in common; and
the third symbol and the fourth symbol having a second shape in common, the second shape being in contrast from the first shape;

the computer is configured to inform the examinee that the set of symbols are part of a recognition system, wherein:
the second symbol is explained to be a thought that produces a conflict in the examinee, as indicated by one or more responses to the plurality of questions from the questionnaire;
the third symbol is explained to be an object of the thought that produces the conflict; and
the fourth and fifth symbols are explained to be a pair of opposing concepts that produce the conflict in the examinee, wherein:
the fifth symbol is explained to be a first concept of the pair, the first concept relating to the second symbol, wherein the fifth symbol is a blindspot in the examinee's mind; and
the fourth symbol is explained to be a second concept of the pair, the second concept relating to the third symbol, wherein the fourth symbol is the examinee's unconsciousness;
the computer is configured to describe the recognition system and a relationship between the symbols and the concepts based on the contrasting shapes and symmetrical positioning of the symbols, wherein the recognition system of the examinee is based on responses from the questionnaire;
the computer, based on the display and the information and description from the computer, is configured to resolve the conflict of the examinee by directing the opposing second concept from the third symbol to the fourth symbol, based on the display and the information and description from the computer; and
the computer is configured to provide a second questionnaire that is used in an analysis to measure treatment efficacy.

12. The system according to claim 11, wherein;
the second symbol and the fifth symbol have a "+" shape; and
the third symbol and the fourth symbol have a "−" shape.

13. The system according to claim 11, wherein the set of symbols further comprises a sixth symbol and a seventh symbol;
the sixth symbol positioned below and to a first side of the third symbol;
the seventh symbol positioned symmetrically across from the sixth symbol, below and to a second side of the third symbol;
the sixth symbol having the second shape in common with the third symbol and the fourth symbol; and
the seventh symbol having the first shape in common with to the second symbol and the fifth symbol.

14. The system according to claim 13, wherein:
the sixth symbol is explained to be a third concept, the third concept relating to the third symbol; and
the seventh symbol is explained to be a fourth concept, the fourth concept relating to the second symbol.

15. The system according to claim 13, wherein:
the sixth symbol has a "−" shape; and
the seventh symbol has a "+" shape.

* * * * *